United States Patent [19]
Oguma et al.

[11] Patent Number: 5,105,841
[45] Date of Patent: Apr. 21, 1992

[54] CLEANING DEVICE FOR CONTACT LENSES

[75] Inventors: Tomio Oguma, Anjo; Mikio Yoshihara, Kariya; Masasi Kai, Toyota; Yasuhiro Aso, Kariya, all of Japan

[73] Assignee: Aisin Seiki Kabushiki Kaisha, Kariya, Japan

[21] Appl. No.: 677,467

[22] Filed: Mar. 29, 1991

[30] Foreign Application Priority Data

Mar. 31, 1990 [JP] Japan ............................ 2-87132
Mar. 31, 1990 [JP] Japan ............................ 2-87133

[51] Int. Cl.⁵ .......................... B08B 3/04; B08B 11/02
[52] U.S. Cl. ................................. 134/57 R; 134/105; 134/186; 134/901; 137/392
[58] Field of Search .............. 134/57 R, 105, 186, 134/901; 137/392

[56] References Cited

U.S. PATENT DOCUMENTS 4,852,592  8/1989  DiGangi et al. ............... 134/901 X
4,986,290  1/1991  Oguma et al. ................. 134/901 X

FOREIGN PATENT DOCUMENTS 2-54416  10/1990  Japan ............................ 134/901

Primary Examiner—Philip R. Coe
Attorney, Agent, or Firm—Oblon, Spivak, McClelland, Maier & Neustadt

[57] ABSTRACT

A cleaning device for contact lenses includes a housing having a cleaning chamber, a stirring device for generating a liquid flow within the cleaning chamber, a heating device for boiling a liquid in the cleaning chamber, a feeding device for feeding the liquid into the cleaning chamber, a discharging device, a feeding amount detecting device for detecting a feeding amount of the liquid which is fed into the cleaning chamber, an operation controlling device for giving a signal to the stirring device, the heating device, the feeding device and the discharging device in response to the feeding amount of the liquid detected by the feeding amount detecting device, respectively and for performing a cleaning process, plural rinsing processes and a boil process. The feeding amount detecting device has a binary output type of liquid level sensor which detects a single liquid level in order to control a first feeding amount in the cleaning process, the last rinsing process and the boil process and a feeding timer which detects a feeding time for controlling a second feeding amount in the other of rinsing processes to be smaller than the first feeding amount. It is thus possible to decrease the consumption rate of the liquid without increasing the size of the device and complicating the structure of the device.

5 Claims, 19 Drawing Sheets

FIG. 19

| | | | |
|---|---|---|---|
| OPERATIONAL INPUT SWITCH | CHANGEOVER SW | | |
| | DISCHARGING SW | | |
| | CLEANING SW | | |
| | BOIL SW | | |
| | START SW | | |
| | CLEARING SW | | |
| INDICATER LAMP | SOFT | | |
| | HARD | | |
| | DISCHARGE | | |
| | CLEAN | | |
| | BOIL | | |
| PROCESS LAMP | CLEAN | | |
| | RINSE | | |
| | BOIL | | |
| | COOLING | | |
| SECURITY PARTS | COVER SWITCH | | |
| | LIQUID LEVEL SENSOR | FIRST ALARM SOUND | |
| | THERMAL SWITCH | | SECOND ALARM SOUND |
| | BUZZER | | |
| CONTROL PARTS | FEEDING VALVE | | |
| | DISCHARGING VALVE | | |
| | AIR-OPENING VALVE | | |
| | MOTOR | | |
| | HEATING MEANS | | |
| TIMER | HARD CLEANING | Tch : 3 min | |
| | SOFT CLEANING | Tcs : 45 sec | |
| | RINSING-CLEANING | Trc : 4 sec | |
| | DISCHARGING | Td : 10 sec | |
| | RINSING-FEEDING ① | Trc1 : 2 sec | |
| | ↑ ② | Trc2 : 2 sec | |
| | ↑ ③ | Trc3 : 10 sec | |
| | BOIL | Tb : 27 min | |
| | COOLING | Tc : 63 min | |

# CLEANING DEVICE FOR CONTACT LENSES

BACKGROUND OF THE INVENTION

1. Field of the Invention

The present invention relates to a cleaning device for contact lenses.

2. Description of the Related Art

In order to clean a contact lens, in general, the contact lens is taken off of a naked eye is held by the palm of a hand or the tip of finger, and is cleaned by dropping a cleaning liquid on its surface, followed by rubbing the contact lens with the tip of the finger. Dirt (particularly fat contained in tears) stained on the surface of a contact lens is thereby removed. After removal from the tip of the finger, the contact lens is rinsed with a rinsing liquid such as distilled water or the like. Thereafter, it is sterilized by boiling it in a preserving liquid such as a physiological saline solution or the like.

Recently, there has been developed a cleaning device for contact lenses which automatically performs a cleaning process, a rinsing process and a boiling process such as described above. The present inventors have found the conventional device to have the following problem. Namely, in the cleaning device for contact lenses of this kind, it is necessary to use the physiological saline solution at least in the rinsing process and the boil process. Furthermore, if the feeding tank of the physiological saline solution is disposed so as to miniaturize the device and to simplify the maintenance of the device, the physiological saline solution must be used in the cleaning process, too.

As mentioned above, in the cleaning device for contact lens of this kind, there are the following drawbacks. Since the consumption rate of the expensive physiological saline solution is large and the burden of the operation for feeding or discharging the physiological saline solution is large for the user, the cost for cleaning the contact lens is increased and the operation for cleaning the contact lens becomes troublesome. Furthermore, since the feeding tank or the discharging tank is enlarged, the device increases in size.

Accordingly, it is desirable to decrease the consumption rate of the physiological saline solution. Furthermore, it is also necessary to simplify and miniaturize the structure of the device, and to improve the durability and ease of maintenance.

Furthermore, it is desirable to use a liquid level sensor in order to automatically perform each process. By use of the liquid level sensor, it is possible to automatically feed a certain amount of the liquid. The conventional liquid level sensor, however, has the following drawbacks. First, of all, it is known to use an electrode-bar type of liquid level sensor in which plural conductive electrode-bars are mounted above the surface of a liquid and detect the fluid level via an electric communication between two electrode-bars. However, since it is necessary to install the electrode-bars onto a pivoting cover member which closes an opening portion of a cleaning chamber, it is necessary to rotate the electrode-bars when the cover member is pivoted and it is also necessary to run the insulated wires from the cover member to the housing. Furthermore, the electrode-bars make maintenance more difficult. On the other hand, in a capacitive type of liquid level sensor in which an electrode-bar formed on the housing is normally contacted with the liquid and which detects the surface of the liquid by a change of contact capacitance of the electrode-bar, it is possible to continuously detect a change of the surface of the liquid, but a circuit for processing the electric signal from the sensor is complicated and becomes expensive.

SUMMARY OF THE INVENTION

It is, therefore, an object of the present invention to provide an improved cleaning device for contact lenses which permits a decrease of the consumption rate of the liquid without increasing the size and complexity of the device.

It is another object of the present invention to provide an improved cleaning device for contact lenses which can minutely control the feeding amount of the liquid without increasing the size and complexity of the device.

It is a further object of the present invention to improve the ease of maintenance of the device.

In order to achieve these and other objects, there is provided a cleaning device for contact lenses which includes a housing having a cleaning chamber which receives contact lenses therein, a stirring means for generating a liquid flow within the cleaning chamber, a heating means for boiling a liquid in the cleaning chamber, a feeding means for feeding the liquid into the cleaning chamber, a discharging means for discharging the liquid out of the cleaning chamber, a feeding amount detecting means for detecting a feeding amount of the liquid which is fed into the cleaning chamber, an operation controlling means for giving a signal to the stirring means, the heating means, the feeding means and the discharging means in response to the feeding amount of the liquid detected by the feeding amount detecting means, respectively and for performing a cleaning process, plural rinsing processes and a boil process. The feeding amount detecting means has a binary output type of liquid level sensor which detects a single liquid level in order to control a first feeding amount in the cleaning process, the last rinsing process and the boil process and a feeding timer which detects a feeding time for controlling a second feeding amount in the other of the rinsing processes to be smaller than the first feeding amount.

BRIEF DESCRIPTION OF THE DRAWINGS

Additional objects and advantages of the present invention will become more apparent from the following detailed description of preferred embodiments thereof when considered with reference to the attached drawings, in which:

FIG. 19 is a timing chart of an embodiment of a cleaning device for contact lenses in accordance with the present invention.

DESCRIPTION OF THE PREFERRED EMBODIMENT

A cleaning device for contact lens constituted in accordance with embodiments of the present invention will be described with reference of the drawings.

Referring to FIG. 1-FIG. 5, there is schematically illustrated a cleaning device for contact lenses which includes a body 100 of molded resin, a body case 200 surrounding an outer circumferential surface of the body 100 and made of molded resin, and a pivoting cover member 300 pivotably supported on an upper portion of the body 100 and made of molded resin. Thereby, a housing of the present invention is constituted by the body 100, the body case 200 and the pivoting cover member 300.

Figure 2:
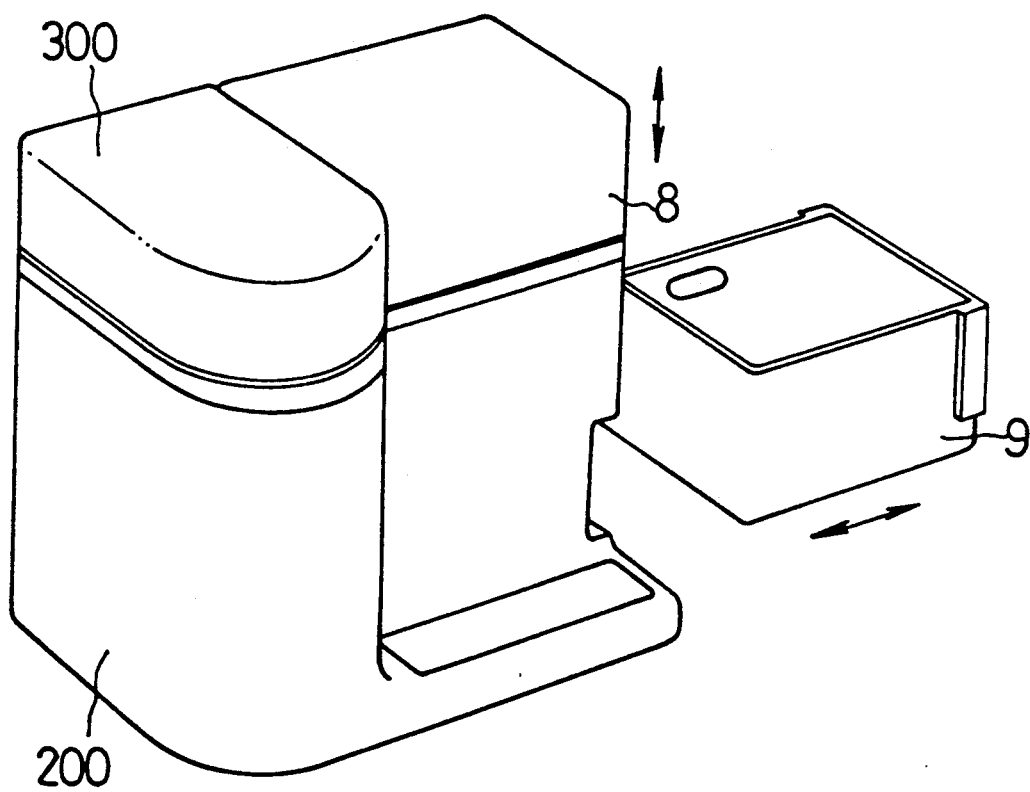
FIG. 2 is a perspective view of an embodiment of a cleaning device for contact lenses in accordance with the present invention.

A cleaning chamber 1 which is open at an upper end portion thereof is formed in the upper portion of the body 100. A stirring means 2 is disposed in a lower portion of the cleaning chamber 1. A heating means 3 which is formed in a bar-shape and a liquid level sensor 20 each extend axially and are positioned at a radially outward portion of the bottom of the cleaning chamber 1. A thermal switch 30 is disposed on a side wall of the cleaning chamber 1. A feeding valve 4, a discharging valve 5, an air-opening valve 6 and an operation controlling means 7 are all received in the body 100. Each valve 4, 5, 6 is comprised of a electromagnetic valve, and an operational panel 102 is disposed on the outside of the lower portion of the body 100 as shown in FIG. 4. On the other hand, a feeding tank 8 is disposed on the upper portion of the body 100 so as to be vertically detachable and a receiving chamber 103 which is defined by the body case 200 is formed at the lower portion of the body 100. The receiving chamber 103 is located under the feeding tank 8 and is opened at one side face thereof. A discharging tank 9 is slidably received in the receiving chamber 103 so as to be detachable in the horizontal direction as shown in FIG. 2 and FIG. 3.

Figure 1:
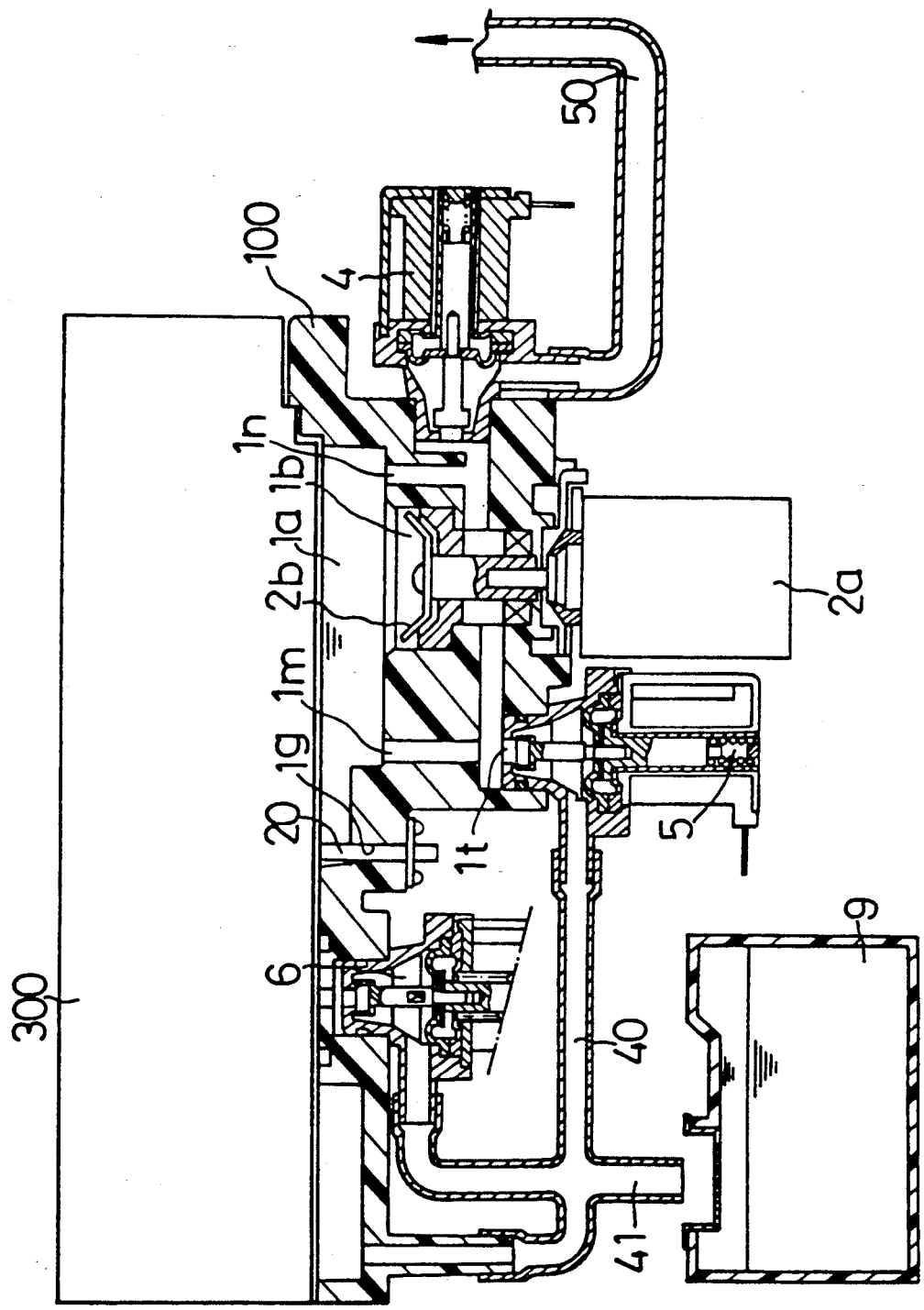
FIG. 1 is a basic cross sectional view of an embodiment of a cleaning device for contact lenses in accordance with the present invention.
Figure 5:
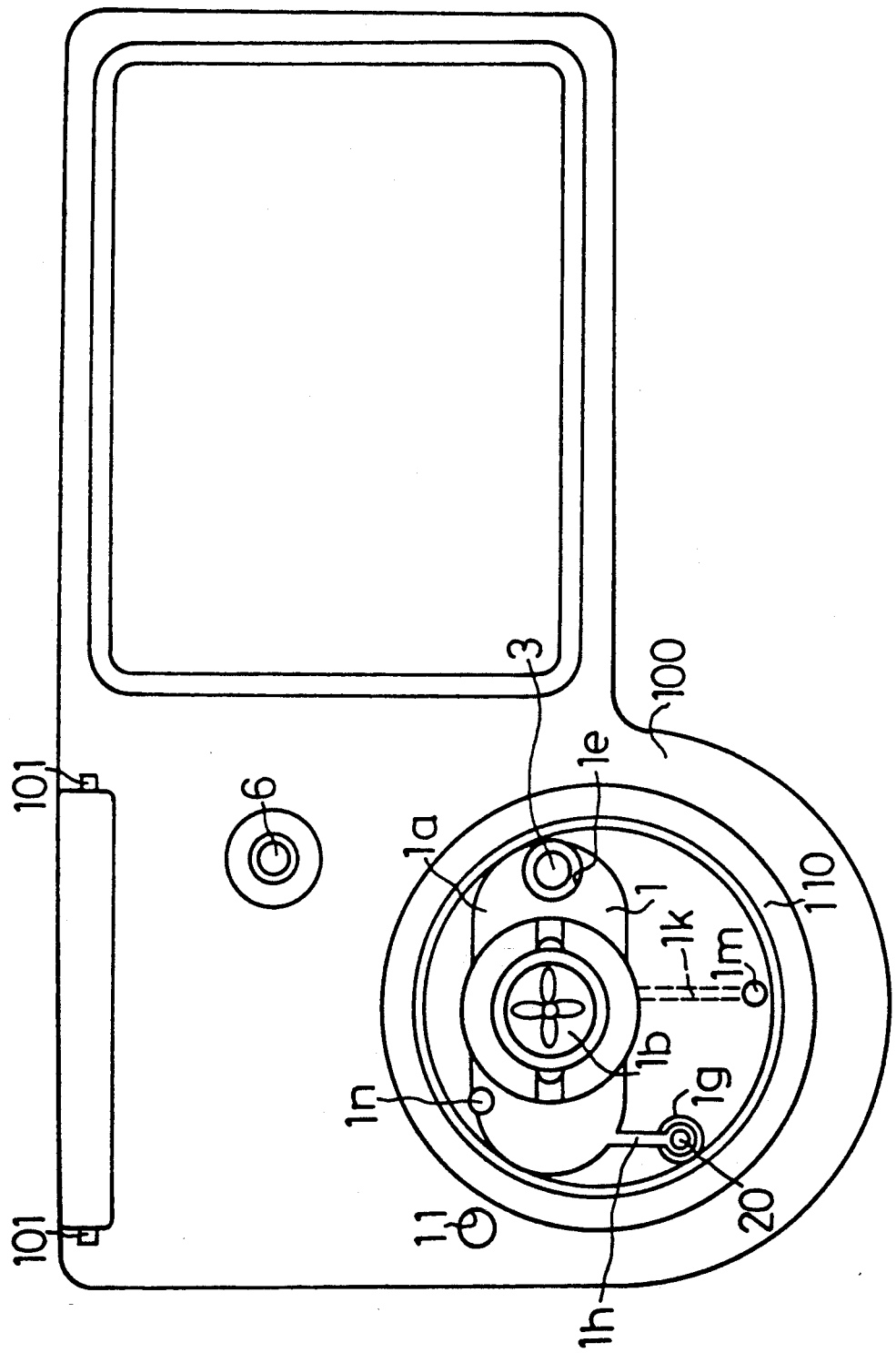
FIG. 5 is a schematic plan view of an embodiment of a cleaning device for contact lenses in accordance with the present invention.

The cleaning chamber 1 is comprised of a container chamber 1a which receives the contact lens therein and a stirring chamber 1b which forms a liquid flow therein. The container chamber 1a is located at an upper portion of the cleaning chamber 1 and has the shape of three overlapping cylinders having axial centers connected in a line as shown in FIG. 5. The stirring chamber 1b is located at a lower portion of the cleaning chamber 1 and a motor 2a is disposed under the stirring chamber 1b. A drive shaft 2c of the motor 2a is liquid-tightly penetrated into the stirring chamber 1b so as to be able to rotate and an impeller 2b is fixed to a top portion of the drive shaft 2c as shown in FIG. 1 and FIG. 3. Thereby, the stirring means 2 is constituted by the motor 2a and the impeller 2b. A groove 110 which surrounds the cleaning chamber 1 is formed in an upper end portion of the body 100 as shown in FIG. 3 and FIG. 5. A sealing ring (not shown) is fitted in the groove 110. A projecting portion (not shown) is formed in an inner surface of the cover member 300. The sealing ring is pressed by the projecting portion so as to seal the cleaning chamber 1 when the cover member 300 is closed.

Figure 20:
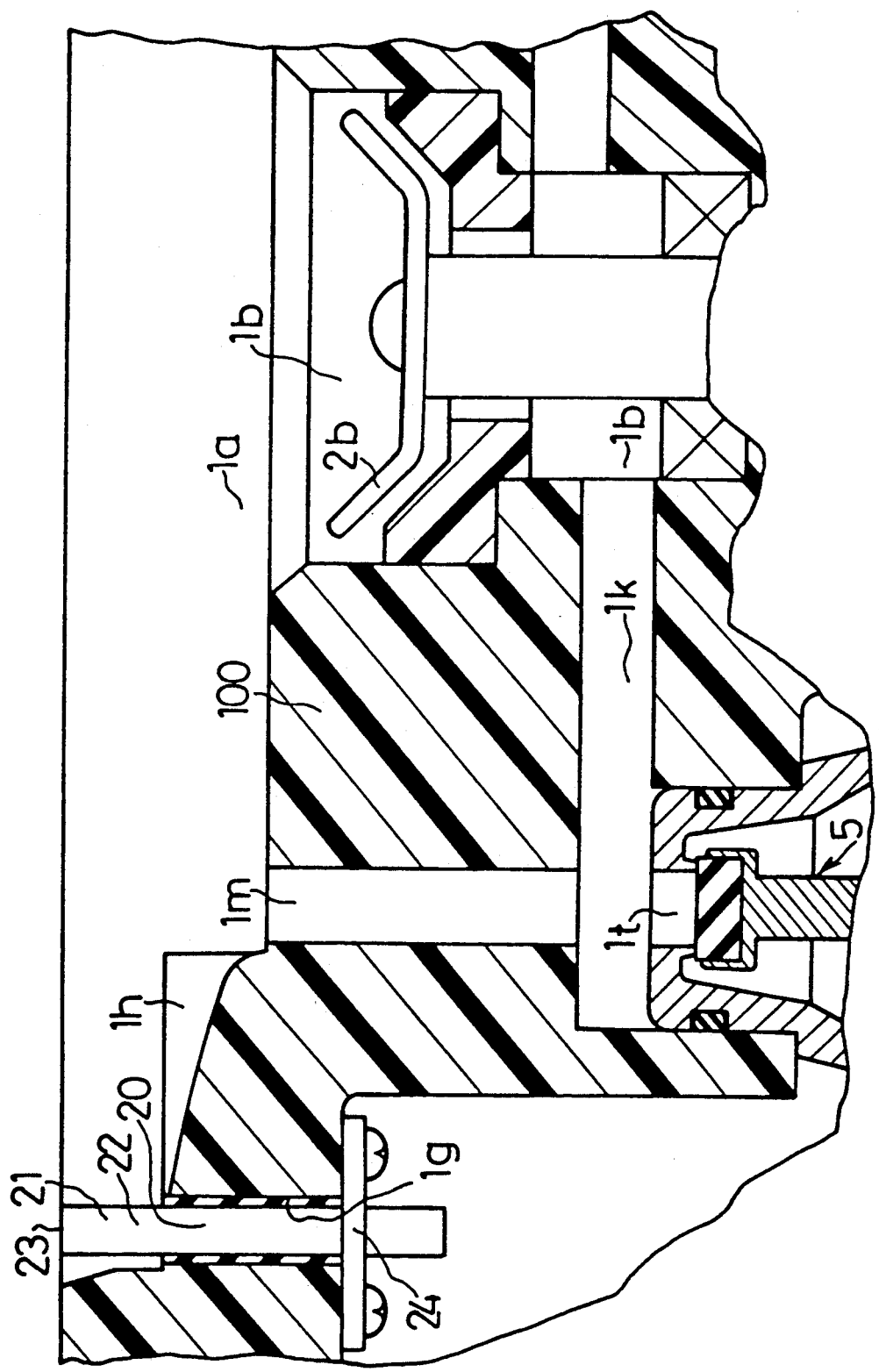
FIG. 20-FIG. 22 are expanded partly sectional views of an embodiment of a cleaning device for contact lens in accordance with the present invention.

In the body 100, a discharging passage 1m is formed near the container chamber 1a and is communicated with a bottom portion of the stirring chamber 1b via a passage 1k which is formed in the body 100 as shown in FIG. 20. A discharging hole 1t is opened into a bottom portion of the discharging passage 1m as shown in FIG. 1 and FIG. 20. Furthermore, a feeding hole 1n is opened into a bottom portion of the container chamber 1a as shown in FIG. 1 and FIG. 5. The discharging hole 1t is communicated with a discharging conduit 40 via the discharging valve 5 and the discharging conduit 40 is communicated with an inlet port of the discharging tank 9 as shown in FIG. 1. The discharging conduit 40 is also communicated with an inlet port of the air-opening valve 6 as shown in FIG. 1 and an outlet port of the air-opening valve 6 communicated with the cleaning chamber 1 via an air-introduction conduit (not shown) which is formed in the cover member 300.

Figure 3:
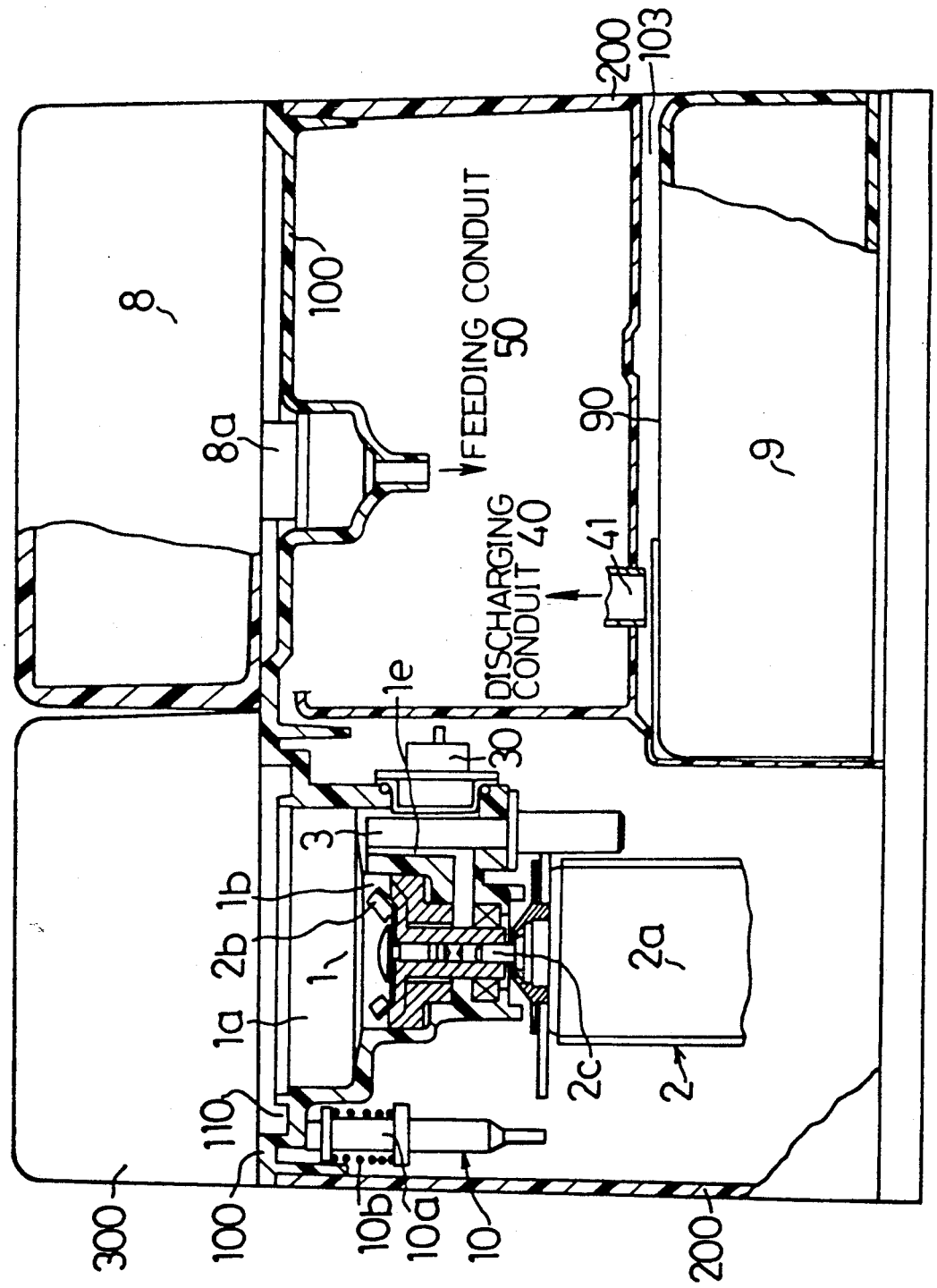
FIG. 3 is a cross sectional front view of an embodiment of a cleaning device for contact lenses in accordance with the present invention.
Figure 4:
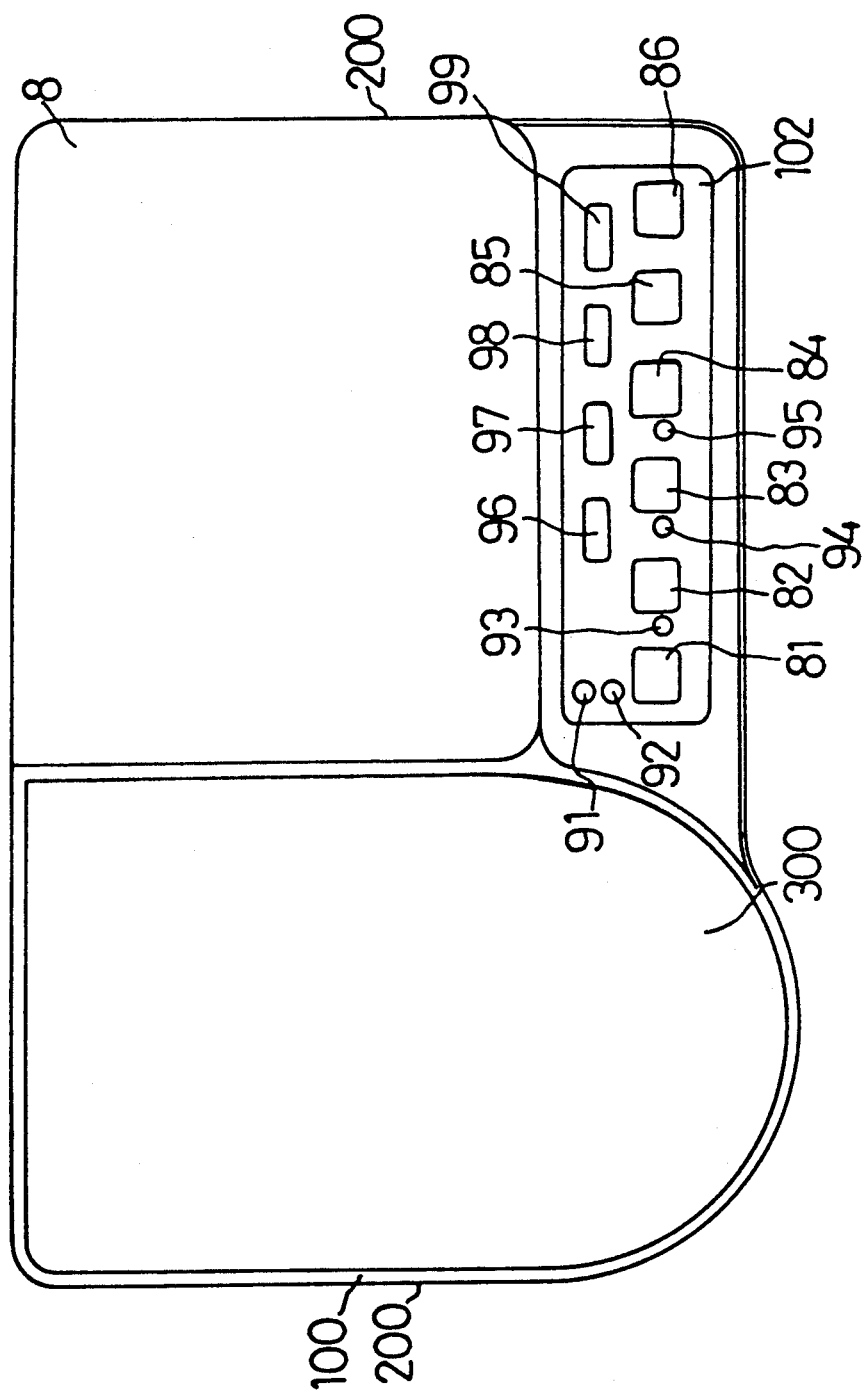
FIG. 4 is a plan view of an embodiment of a cleaning device for contact lenses in accordance with the present invention.

The feeding hole 1n is communicated with a feeding conduit 50 via the feeding valve 4 as shown in FIG. 1 and the feeding conduit 50 is connected with a drop-away hole 8a of the feeding tank 8 as shown in FIG. 3.

Figure 21:
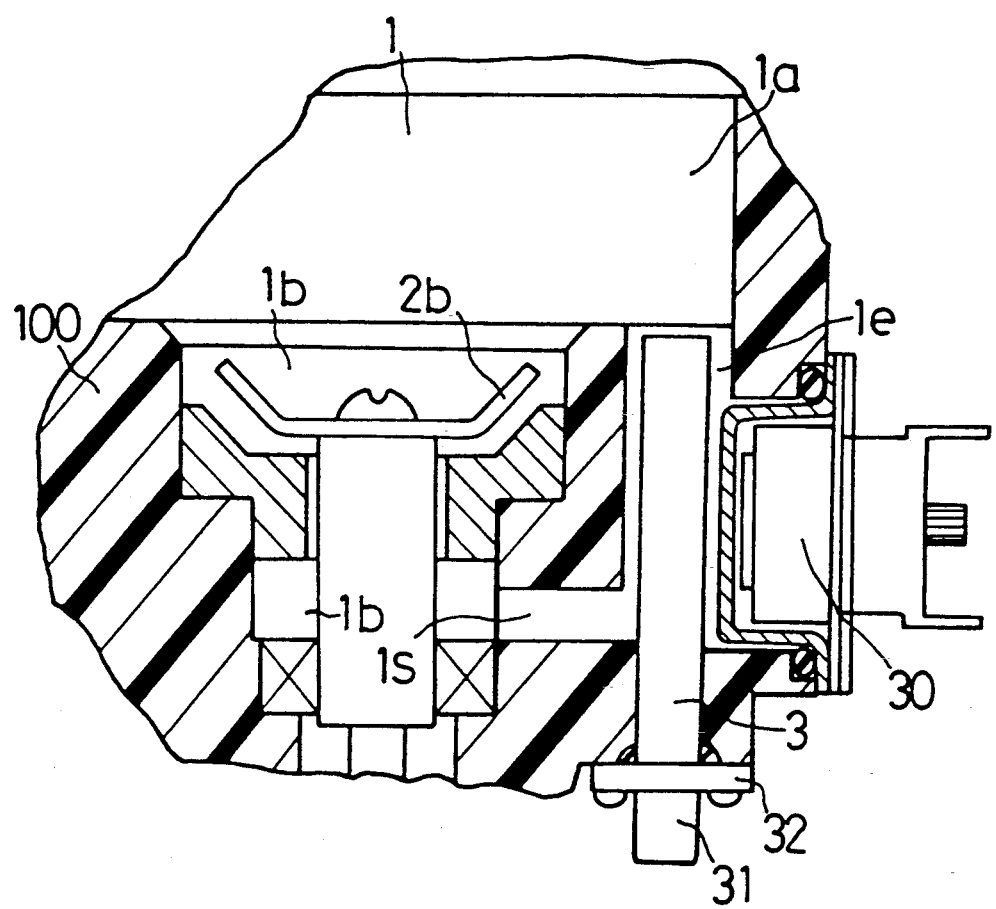
Figure 22:
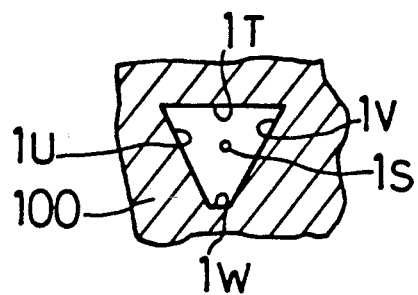

A heat chamber 1e is formed near a circumferential end portion of the stirring chamber 1b as shown in FIG. 1 and FIG. 21. An upper end of the heat chamber 1e is communicated with the container chamber 1a and a lower end of the heat chamber 1e is communicated with a lower portion of the stirring chamber 1b via a passage 1s which is formed in body 100 as shown in FIG. 21. The heater means 3 is mounted on a bottom portion of the heat chamber 1e and is fixed to the body 100 by a supporting ring 32. The heat chamber 1e has a opening portion at a side wall thereof and a bimetal-type of thermal switch 30 is fitted in this opening portion. The thermal switch 30 which is reset by a manual operation functions as a switch for preventing overheating of the heating means 3. The thermal switch 30 acts as a circuit breaker to interrupt current to the heating means 3 when the heat chamber 1e is overheated.

The heating means 3 heats the liquid in the cleaning chamber 1 and is constituted by a cylindrical case 31 which is made of stainless steel and an insulated nichrome exothermic wire (not shown) which is received in the cylindrical case 31. The nichrome exothermic wire is insulated by the insulator and a terminal (not shown) is disposed in a lower end of the cylindrical case 31 in order to flow the current to the nichrome exothermic wire.

On the operational panel 102 are mounted a change-over switch 81 which is changed in response to a type of contact lens to be cleaned, for example soft contact lens or hard contact lens, a discharging switch 82, a cleaning switch 83, a boiling switch 84, start switch 85 and a clearing switch 86. In switches 82-85 are disposed operational indicators 93-95. When each switch 82 (83, 84, 85) is pushed, each operational indicator 93 (94, 95) lights and continues to light until a series of processes is finished or the clearing switch 86 is pushed. A soft selection indicator 91 and a hard selection indicator 92 are disposed near the clearing switch 86. Furthermore, process indicators 96-99 which indicate the advancing of a process are disposed on the operational panel 102. A buzzer (not shown) is disposed behind the operational panel 102.

A cover switch 10 is disposed in the upper portion of the body 100 as shown in FIG. 3. The cover switch 10 is constituted by a sliding bar 10a which is vertically slidable, a spring 10b which is fitted on an outer circumferential surface of the sliding bar 10a and which upwardly urges the sliding bar 10a and a limit switch (not shown) which is adjacent to a lower end portion of the sliding bar 10a. An upper end portion of the sliding bar 10a is fitted in a cover switch hole 11 which is opened to an upper surface of the body 100 as shown in FIG. 5. On the other hand, a projection (not shown) is formed in the rotary cover member 300 in order to push the sliding bar 10a. Thereby, when the cover member 300 is closed, the sliding bar 10a is pushed downwardly by the projection of the cover member 300 and the limit switch (not shown) is operated by the lower end portion of the sliding bar 10a.

A sensor chamber 1g which is adjacent to the container chamber 1a is formed in the upper portion of the body 100 as shown in FIG. 20. The sensor chamber 1g is communicated with a deep portion of the container chamber 1a via a slant groove 1h which is formed in the body 100.

In the sensor chamber 1g, the liquid level sensor 20 which has a bar shape is vertically mounted on a bottom portion thereof. The liquid level sensor 20 is composed of a stainless steel bar 21 which is coated with PTFE (polytetrafluoroethylene) on all outer circumferential surface thereof. The stainless steel bar 21 constitutes a bar-shaped electric conductor with only top portion 23 thereof exposed. Accordingly, when the liquid reaches the top portion 23, electrical current from the top portion 23 is conducted to the grounded cylindrical case 31 of the heating means 3 via the liquid. A lower portion of the stainless steel bar 21 is liquid-tightly penetrated into the bottom portion of the sensor chamber 1g and is fixed to the body 100 via a supporting ring 24 which is fitted thereon. A bottom portion of the stainless steel bar 21 functions as an output terminal of the liquid level sensor 20.

Figure 9:
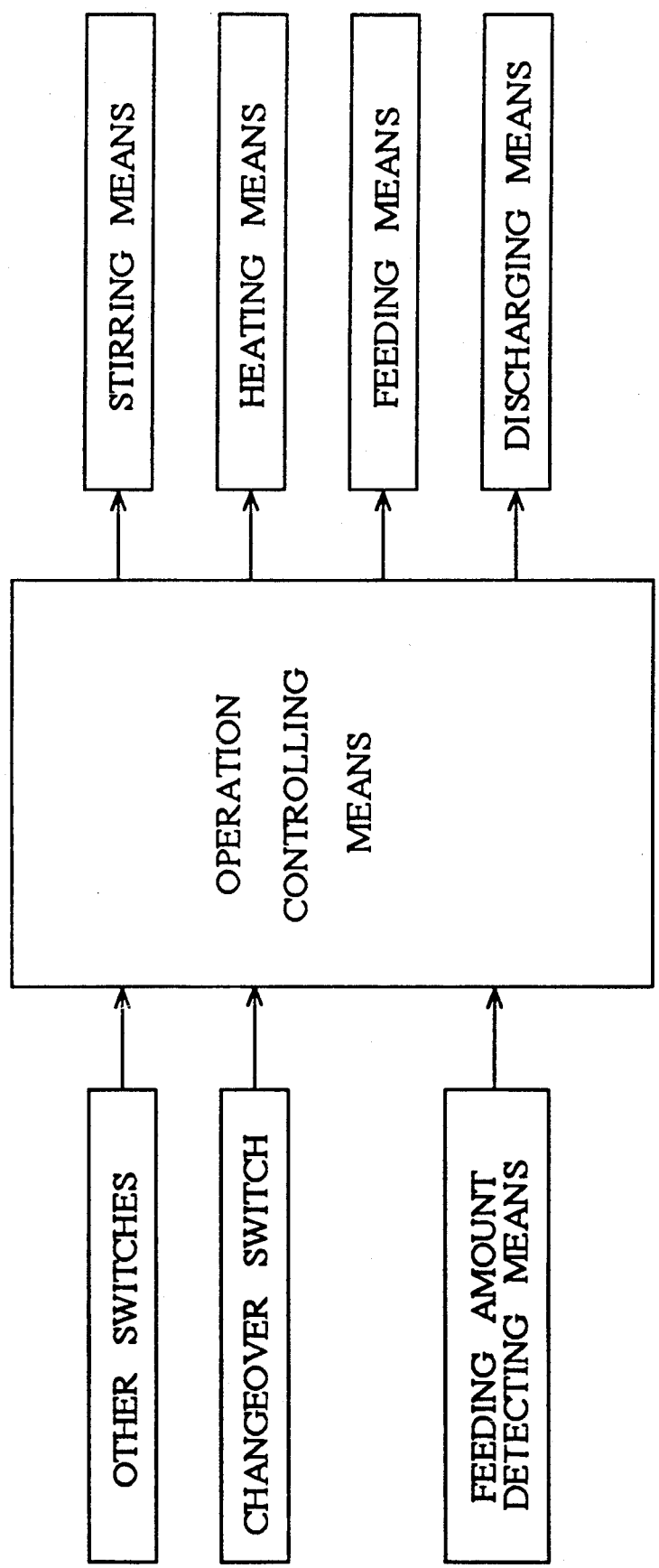
FIG. 9 is a basic block diagram of an embodiment of a microcomputer in a cleaning device for contact lenses in accordance with the present invention.
Figure 10:
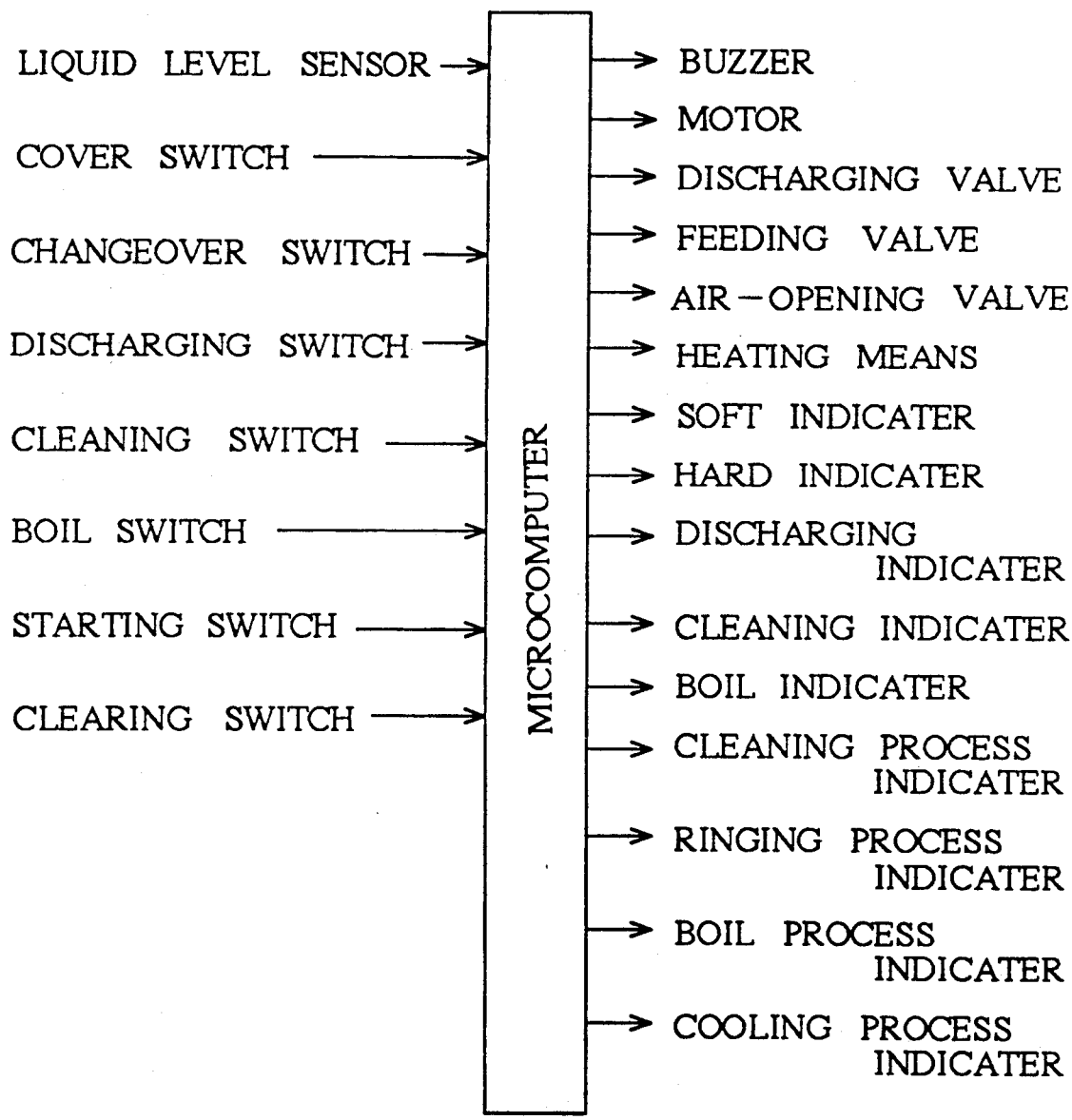
FIG. 10 is a more detailed block diagram of an operation controlling means in an embodiment of a cleaning device for contact lenses in accordance with the present invention.

The operation controlling means 7 is composed of an electric controlling device which includes a microcomputer as shown in FIG. 9 and FIG. 10. The operation controlling means 7 receives signals from the cover switch 10, the liquid level sensor 20 and plural switches 81-86 and operates the motor 2a, the feeding valve 4, the discharging valve 5, the air-opening valve 6 and the heating means 3. The microcomputer includes a feeding timer of the present invention built-in.

The operation controlling means 7 includes resisters which have 1 bit of data capacity, respectively. Memory states of each of these resisters is used as a flag. Each flag is set by pushing a respective one of the switches (82-86) and is reset by pushing the clearing switch 86 or finishing a series of processes. The changeover switch 81 is reset to a soft-range by pushing the each switch (82-86) and is reset by pushing the clearing switch 86 or finishing a series of processes. Furthermore, the changeover switch 81 is set to a hard-range by pushing it when the soft-range is chosen and is reset to the soft-range by pushing it when the hard-range is chosen. A feeding flag and a rinsing flag are set by a program of the operation controlling means 7, respectively, and a discharging flag is set by a program of the operation controlling means 7 or pushing the discharging switch 82.

Figure 6:
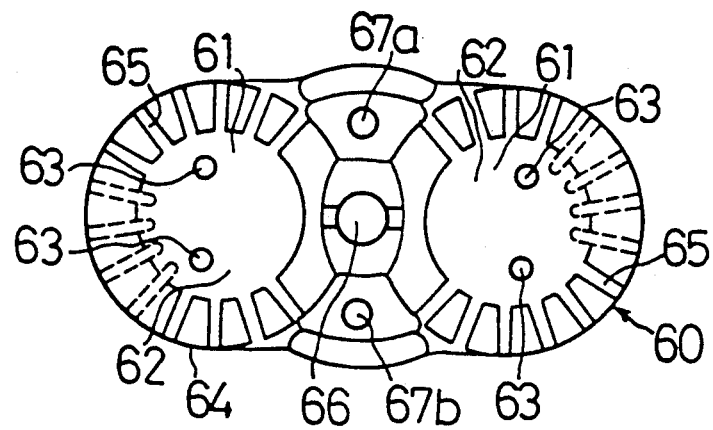
FIG. 6 is a plan view of a case body of a lens case in an embodiment of a cleaning device for contact lenses in accordance with the present invention.
Figure 7:
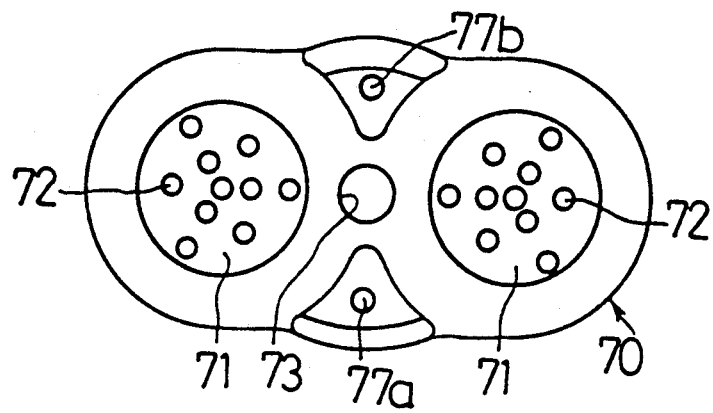
FIG. 7 is a plan view of a cover member of a lens case in an embodiment of a cleaning device for contact lenses in accordance with the present invention.
Figure 8:
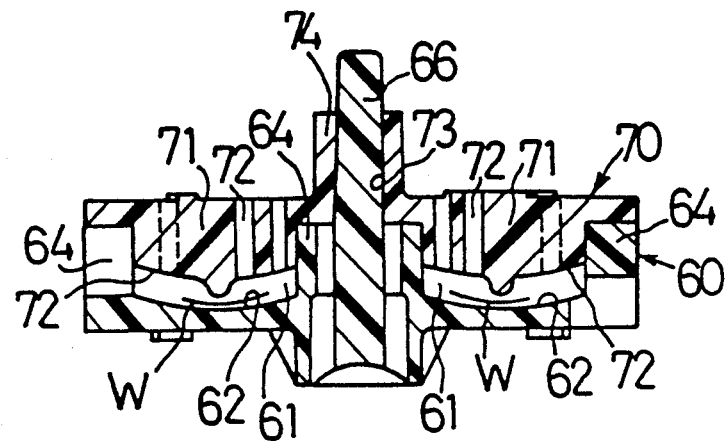
FIG. 8 is a cross sectional view of a lens case in an embodiment of a cleaning device for contact lenses in accordance with the present invention.

A lens case 400 is composed of a container body 60 and a cover 70 which is fitted in the container body 60 as shown in FIG. 6-FIG. 8. The lens case 400 is set in the cleaning chamber 1 so as not to be caused to float by the liquid flow. Therefore, the lens case 400 has a profile similar to that of the container chamber 1a and is smaller than the volume of the container chamber 1a. The container body 60 is provided with two lens receiving chambers 61, 61 and is closed by fitting the cover 70 therein. Plural holes are formed in the container body 60 and the cover 70, thereby the liquid-communication between the lens receiving chambers 61 and cleaning chamber 1 is ensured.

Each lens receiving chamber 61 has a cylindrical shape, respectively and the cover 70 is fitted in opening portions of each lens receiving chamber 61 so as to cover each lens receiving chamber 61. In a bottom portion 62 of each lens receiving chamber 61 are formed plural penetrating holes 63.

Furthermore, plural penetrating holes 64 are radially formed in each side wall 64 of the lens receiving chambers 61. A projecting portion 66 which has a long-bar shape is formed in a center portion of the container body 60. A pair of fitting portions 67a, 68b are formed in the container body 60 so as to nip the projecting portion 66. The fitting portion 67a is composed of a circular hole and the fitting portion 67b is composed of a circular bar.

On the other hand, two circular projecting portions 71, 71 which are fitted in the lens receiving chambers 61, 61, respectively are formed in the cover 70. An inner surface of each circular projecting portion 71 is spherically formed so as to fit a shape of contact lens W. Plural penetrating holes 72 are formed in each circular projecting portion 71, respectively. Furthermore, a tube portion 74 having a hole 73 is formed in a center portion of the cover 70 and the projecting portion 66 of the container body 60 is fitted in the hole 73. Furthermore, a pair of fitting portions 77a, 77b are formed in the cover 70 so as to nip the tube portion 74. The fitting portion 77b is composed of a circular hole which is fitted on the facing portion 67b of the container body 60 and the fitting portion 77a is composed of a circular bar which is fitted into the fitting portion 67a of the container body 60.

Figure 17:
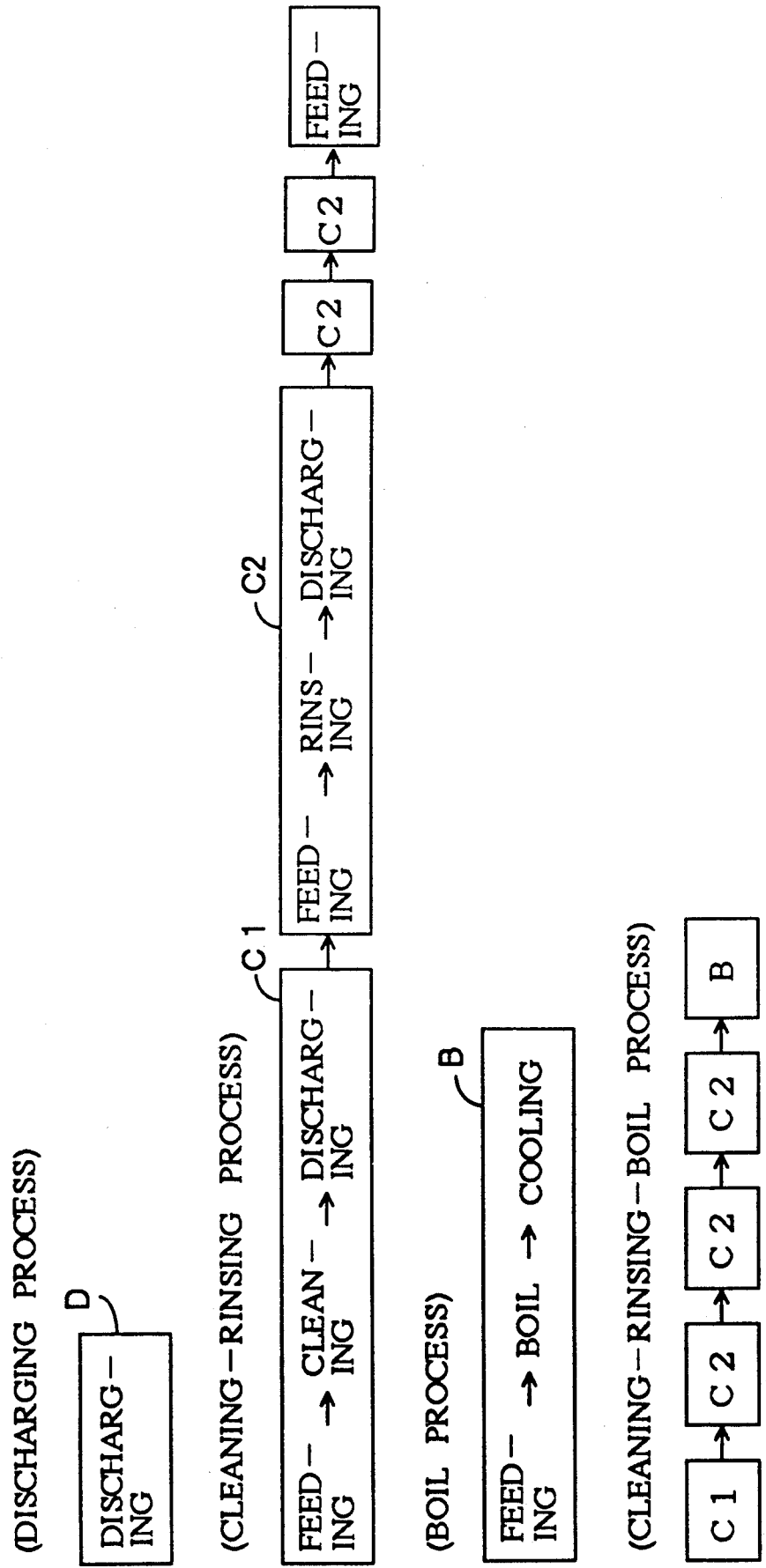
FIG. 17 is a flow diagram of an embodiment of a cleaning device for contact lenses in accordance with the present invention.

The above-described embodiment of the cleaning device for contact lens operates as follows. The operation of this cleaning device is composed of a discharging operation, a feeding operation, a cleaning operation, a rinsing operation and a boiling operation. The feeding operation, the cleaning operation and the discharging operation are performed in turn in a cleaning process C1 as shown in FIG. 17. Furthermore, the feeding operation, the rinsing operation and the discharging operation are repeatedly performed in turn three times in rinsing processes C2. In a boil process B, the feeding operation, the boil operation and the discharging operation are performed in turn. Furthermore, only the discharging operation is performed in a discharging process D.

In practice the operation controlling means 7 is constituted so as to be able to perform the discharging process D, the boil process B, a cleaning-rinsing process which combines three rinsing processes C2 and a feeding operation with a cleaning process C1, and a cleaning-rinsing-boil process which combines three rinsing processes C2 and the boil process B with the cleaning process C1 as shown in FIG. 17. Now, the cleaning-rinsing process sequentially performs the cleaning process C1, the rinsing processes C2 and the feeding operation. The cleaning-rinsing-boil process sequentially performs the cleaning process C1, the rinsing processes C2 and the boil process B.

The cleaning-rinsing process is generally used in an automatic cleaning of a hard contact lens (of course, it may be used in automatic cleaning of a soft contact lens which does not require boiling). The cleaning-rinsing-boil process is generally used in an automatically cleaning of a soft contact lens.

Now, when a portable case for contact lenses is to be boiled with the contact lenses therein, first of all the contact lenses are received in the lens case 400 and the cleaning-rinsing process is performed. Next, the contact lenses are sealed up in the portable case with a physiological saline solution and the boil process B is performed. Thereby, it is possible to have the contact lenses in the portable case in an aseptic condition after the boil process B is performed. Of course, it is possible to perform the boil process B only for a portable case of the hard contact lenses. In this case, the cleaning-rinsing process is performed for the hard contact lenses themselves.

Each process is performed in accordance with the following operations, respectively. Each routine is repeated with a period of about 1 msec (0.01 sec) by the microcomputer of the operation controlling means 7. A setting operation of a boil flag is performed as follows.

Figure 16:
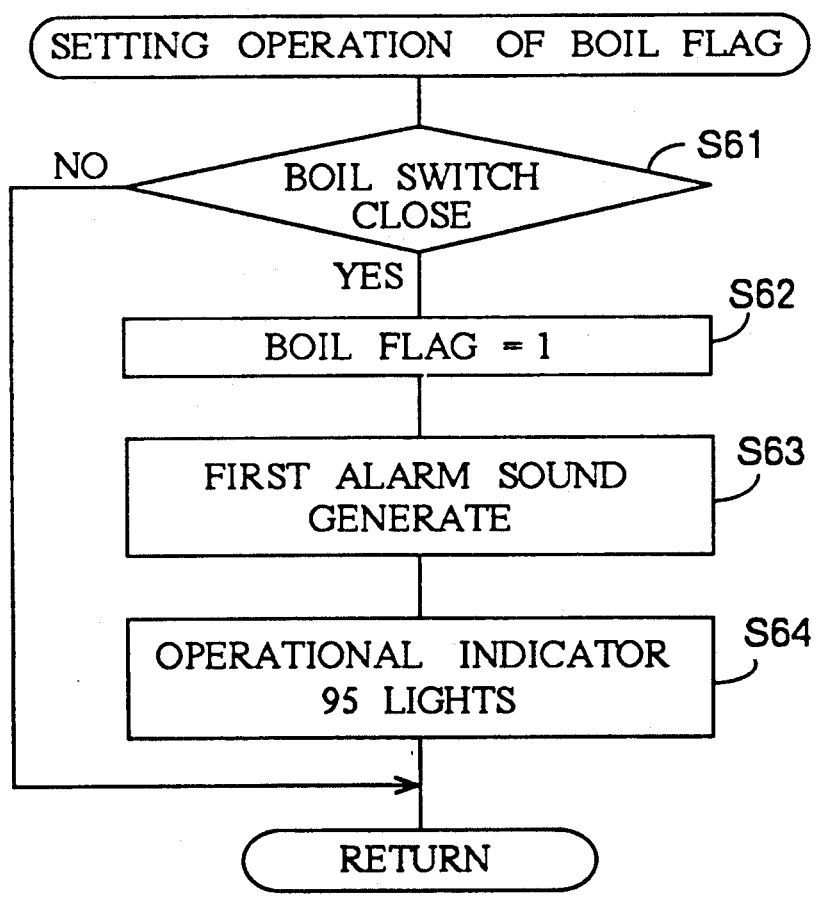

Referring to FIG. 16, first of all a condition of the boil switch 84 is judged in a step S61. If a closure of the boil switch 84 is judged in the step S61, a step S62 is performed and the boil flag is set in the step S62.(the boil flag becomes "1".) Now, if the boil switch 84 is not closed, the step S62 is not performed and a sub routine for the setting operation of the boil flag is stopped so as to return to a main routine. Otherwise, in a step S63, a signal is sent to the buzzer in order to generate a first alarm sound which warns a user of a boil designation. Next, a boil operational indicator 95 is lighted in a step S64 and operation returns to this main routine. This first alarm sound is not generated by setting of other flags.

According to this setting operation of a boil flag, even though the boil switch 84 is pushed by mistake under the condition in which a hard contact lens is received in the cleaning chamber 1, it is possible to clearly warn the user of the mistake.

Figure 11:
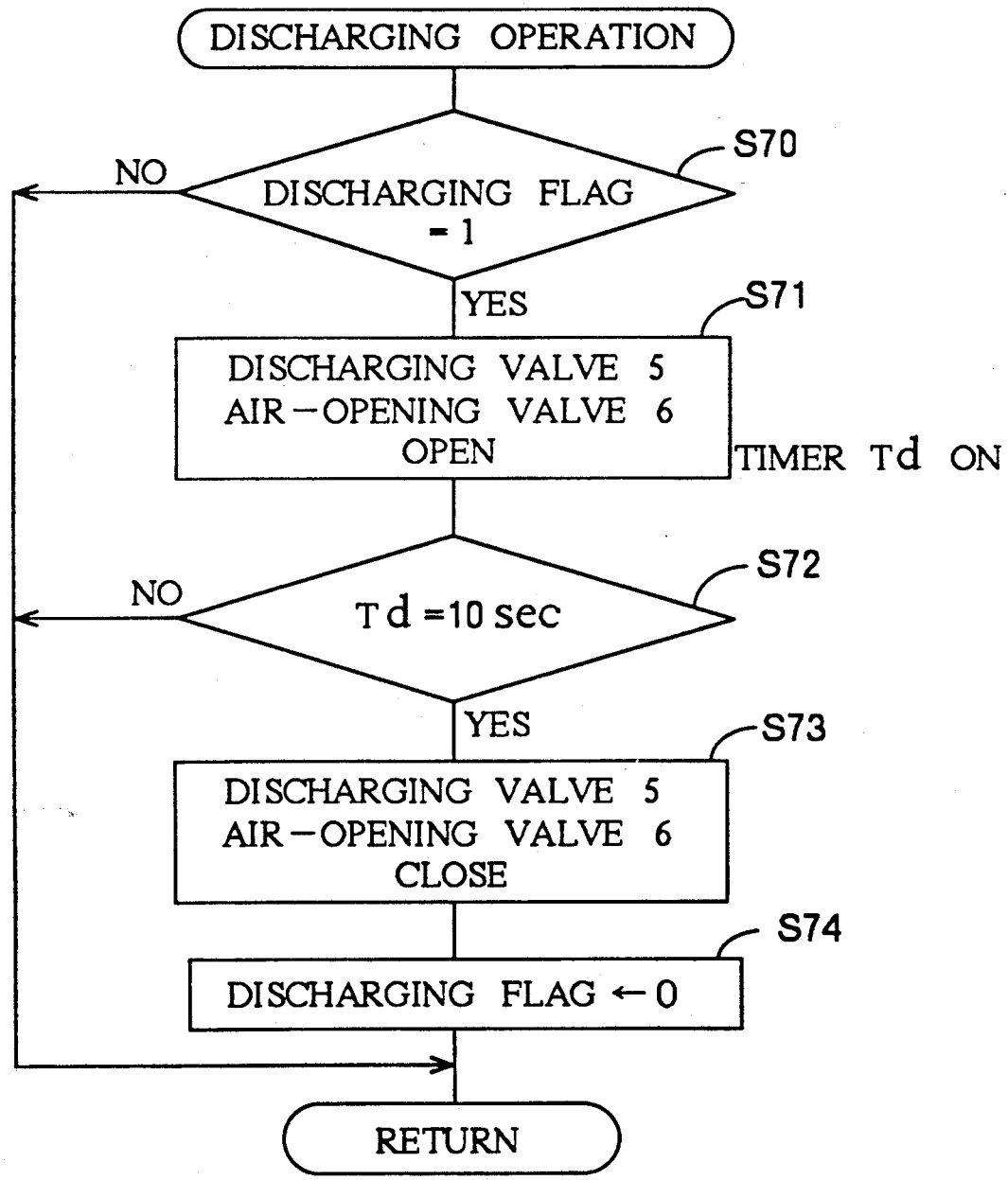
FIG. 11-FIG. 16 are flow charts of sub-routines of an operation controlling means in an embodiment of a cleaning device for contact lenses in accordance with the present invention.

The discharging operation is performed as shown in FIG. 11. Referring to FIG. 11, first of all a condition of a discharging flag is judged in a step S70. If a setting of the discharging flag is judged in the step S70 (the discharging flag is "1"), a step S71 is performed and the discharging valve 5 and the air-opening valve 6 are opened, respectively. Now, if the discharging flag is not set, the step S71 is not performed and a sub routine for the discharging operation is stopped so as to return to the main routine. Otherwise, in a step S72, a time during which the discharging valve 5 and the air-opening valve 6 are opened is counted. If the time has reached 10 minutes, a step S73 is performed and the discharging valve 5 and the air-opening valve 6 are closed, respectively. Now, if the time is shorter than 10 minutes, the step S73 is not performed and the sub routine for the discharging operation is stopped so as to return to the main routine. Otherwise, a step S74 is performed and the discharging flag is reset (the discharging flag becomes "0").

Figure 12:
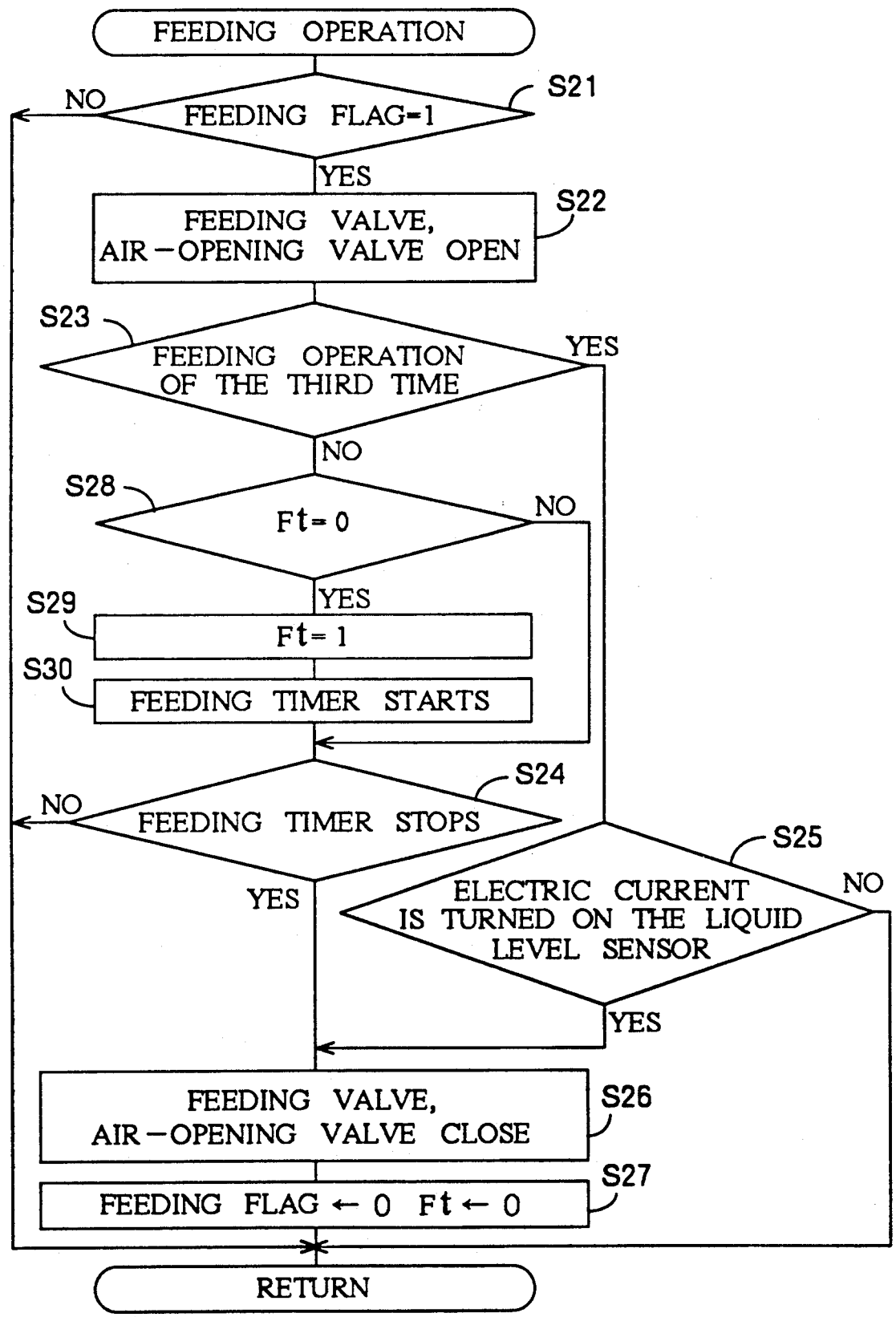

The feeding operation is performed as shown in FIG. 12. Referring to FIG. 12, first of all a condition of a feeding flag is judged in a step S21. If a setting of the feeding flag is judged in the step S21 (the feeding flag is "1"), a step S22 is performed and the feeding valve 4 and the air-opening valve 6 are opened, respectively. Now, if the feeding flag is not set, the step S22 is not performed and a sub routine for the feeding operation is stopped so as to return to the main routine. Otherwise, in a step S23, a condition of whether the feeding operation is performed for the feeding operation of the first time and the second time in the rinsing process C2 is judged (referring to FIG. 17). If the first and second or third feeding operation is being performed for the first or second rinsing process C2, a step S28 is performed and a condition of a feeding timer start flag Ft is judged. If the feeding timer start flag Ft is not set (the flag Ft is "0"), the feeding timer start flag Ft is set (the flag Ft becomes "1") in a step S29 and the feeding timer is started in a step S30. Next, a condition of whether the feeding timer has ended or not is judged in a step S24. Now, if the feeding timer start flag Ft is not "0", the step S29 and the step S30 are not performed and the step S24 is performed. In the step S24, if the end of the feeding timer is judged, a step S26 is performed and the feeding valve 4 and the air-opening valve 6 are closed. Next, in a step S27, the feeding flag and the feeding timer start flag Ft are reset to "0". Now, if the end of the feeding timer is not judged in the step S24, the sub routine for the feeding operation is stopped so as to return to the main routine.

On the other hand, in the step S23, if the feeding operation in the first or second rinsing process C2 is not performed but is performed for the cleaning process C1 or the feeding operation for the third rinsing process C2 or the feeding operation in the boil process B, the step S28 is not performed and a step S25 is performed. Instead, in the step S25, a condition of whether the electric current is turned on in the liquid level sensor 20 is judged. If the electric current is turned on in the liquid level sensor 20, the step 26 is performed. If the electric current is not turned on the liquid level sensor 20, the sub routine for the feeding operation is stopped so as to return to the main routine. The liquid sensor 20 sends a signal to the operation controlling means 7 when the liquid level exceeds a full level. The operation controlling means 7 closes the feeding valve 4 in response to this signal. The feeding timer is set to an operational time of about 2 seconds. The cleaning chamber 1 is fed up to one third of the full level in a feeding operation of 2 seconds. Now, the steps S30, S24 and S25 correspond to a feeding amount controlled by controlling means in FIG. 9.

As mentioned above, since the feeding amount is reduced in the feeding operation of the first and second rinsing processes C2, it is possible to perform the rinsing operation sometimes with a certain small amount of liquid while effectively eliminating dirt or bubbles. Under the condition which an expected physiological saline solution is used in the rinsing operation and in which a volume of the feeding tank 8 and a volume of the discharging tank 9 is limited as shown in this embodiment, it is possible to effectively save the physiological saline solution by the performance of some of the plural rinsing operations with a small amount of liquid. Furthermore, in this embodiment, since the last rinsing process C2 is performed at full liquid level, the dirt and the bubbles which remain in the cleaning chamber 1 and the lens case 400 float away. Therefore, it is possible to prevent the adherence of floating dirt and the bubbles to the contact lens W or the lens case 400 and it is possible to prevent the invasion of the dirt and the bubble into the holes of the lens case 400. Also, since the feeding amount in the feeding operation of the first and second rinsing process C2 is controlled by the feeding timer, it is possible to simplify the feeding amount control.

Figure 13:
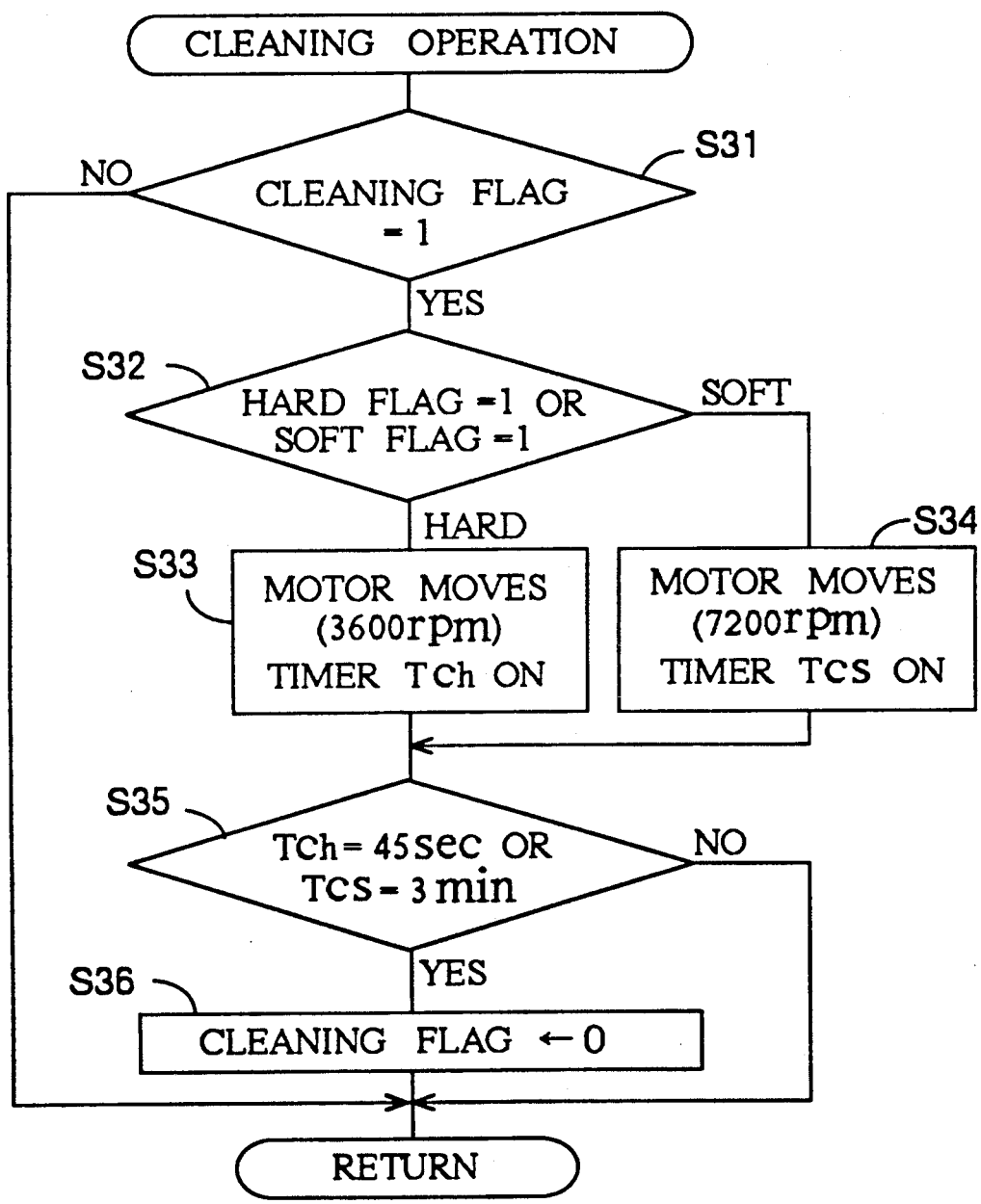

The cleaning operation is performed as shown in FIG. 13. Referring to FIG. 13, first of all a condition of a cleaning flag is judged in a step S31. If a setting of the cleaning flag is judged in the step S31 (the cleaning flag is "1"), a step S32 is performed and a condition of whether a hard flag is set or the soft flag is set is judged in a step S32. Now, if the cleaning flag is not set, the step S32 is not performed and a sub routine for the cleaning operation is stopped so as to return to the main routine. In the step S32, if a setting of the hard flag is judged, a step S33 is performed and a motor rotational speed control circuit (not shown) which the operation controlling means 7 has built-in is operated so as to rotate the motor 2a with the speed of 3600 rpm. Furthermore, a cleaning timer (not shown) which the operation means 7 has built-in is set with a time of 45 seconds and is started. Now, if a setting of the soft flag is judged in the step S32, a step S34 is performed and the motor rotational speed control circuit (not shown) which the operation controlling means 7 has built-in is operated so as to rotate the motor 2a with the speed of 7200 rpm. Furthermore, a cleaning timer (not shown) which the operation means 7 has built-in and is to set the time of 3 minutes is started. Since a variable speed control of the motor 2a and the motor rotational speed control circuit (not shown) are well-known, the description thereof is omitted herein. Next, a step S35 is performed and a condition of whether the cleaning timer steps S33, S34 has stopped is judged. In the step S35, if the stoppage of the cleaning timer is judged, a step S36 is performed and the cleaning flag is set to "0". Now, if the end of the cleaning timer is not judged in the step S35, the step S36 is not performed and the sub routine for the cleaning operation is stopped so as to return to the main routine.

Figure 14:
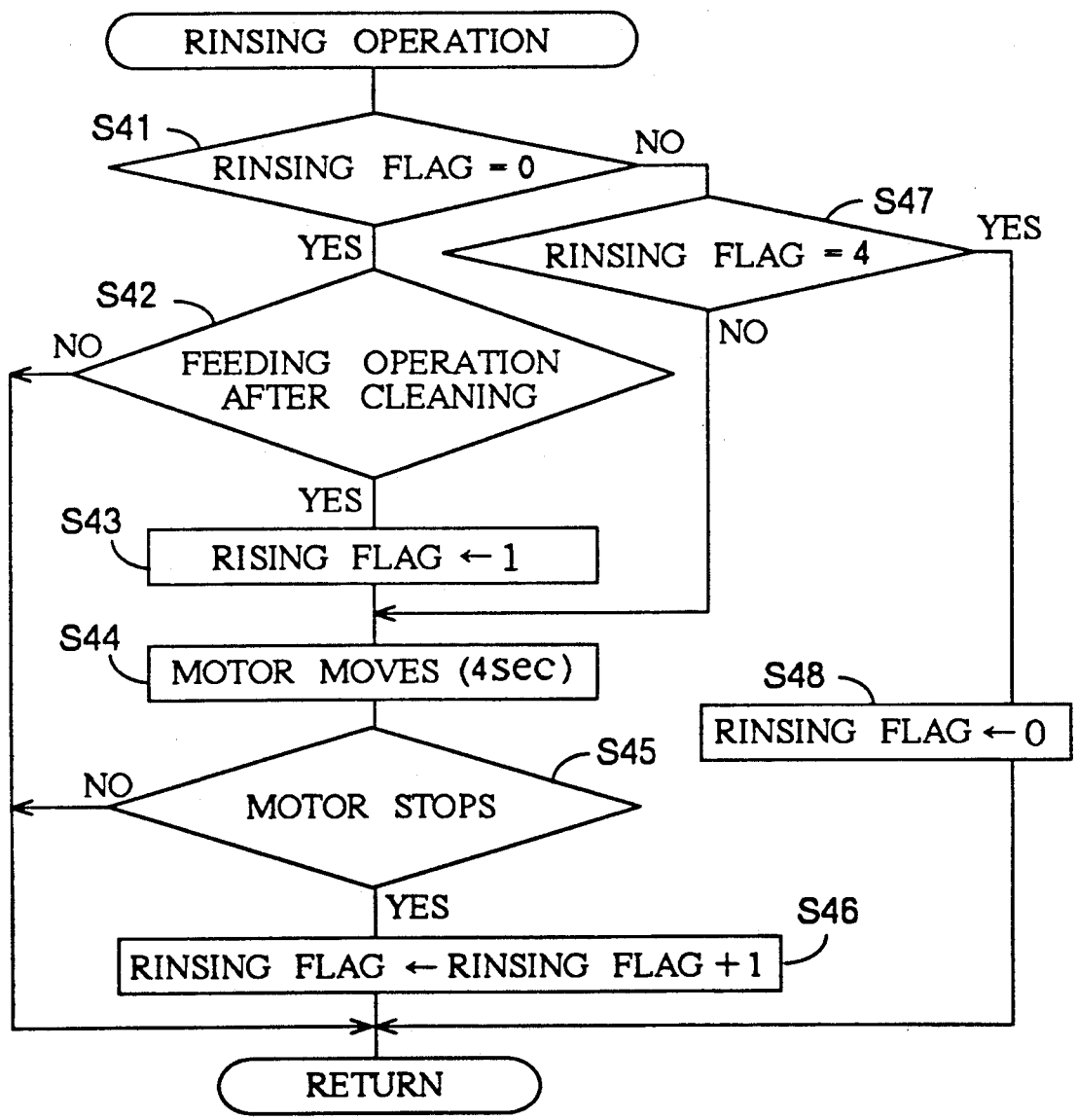

The rinsing operation is performed as shown in FIG. 14. Referring to FIG. 14, first of all a condition of a rinsing flag is judged in a step S41. If a setting of the rinsing flag is not judged in the step S41 (the rinsing flag is "0"), a step S42 is performed and a condition of whether the feeding operation was performed after the cleaning operation or not is judged. If the feeding operation was performed after the cleaning operation, a step 43 is performed and the rinsing flag is set (the rinsing flag becomes "1"). Now, if the feeding operation was not performed after the cleaning operation, a step 43 is not performed and the sub routine for the rinsing operation is stopped so as to return to the main routine. Next, a step S44 is performed and the motor 2a is moved for 4 seconds. Furthermore, in the step S44, a rinsing timer (not shown) which the operation controlling means 7 has built-in is started. Thereafter, a step S45 is performed and a condition of whether the rinsing timer has stopped or not is judged. If the stopping of the rinsing timer is judged in the step S45, a step S46 is performed and "1" is set for the rinsing flag. Now, if the end of the rinsing timer is not judged in the step S45, the step S46 is not performed and the sub routine for the rinsing operation is stopped so as to return to the main routine.

On the other hand, if the setting of the rinsing flag is judged in the step S41, a step S47 is performed and a condition of whether the rinsing flag is "4" or not is judged. If the rinsing flag is not "4", the step S44 is performed. If the rinsing flag is "4", a step S48 is performed and the rinsing flag is reset (the rinsing flag becomes "0"). When the step S48 is performed, the main routine is performed.

As mentioned above, the rinsing operation is performed three times in turn.

Figure 15:
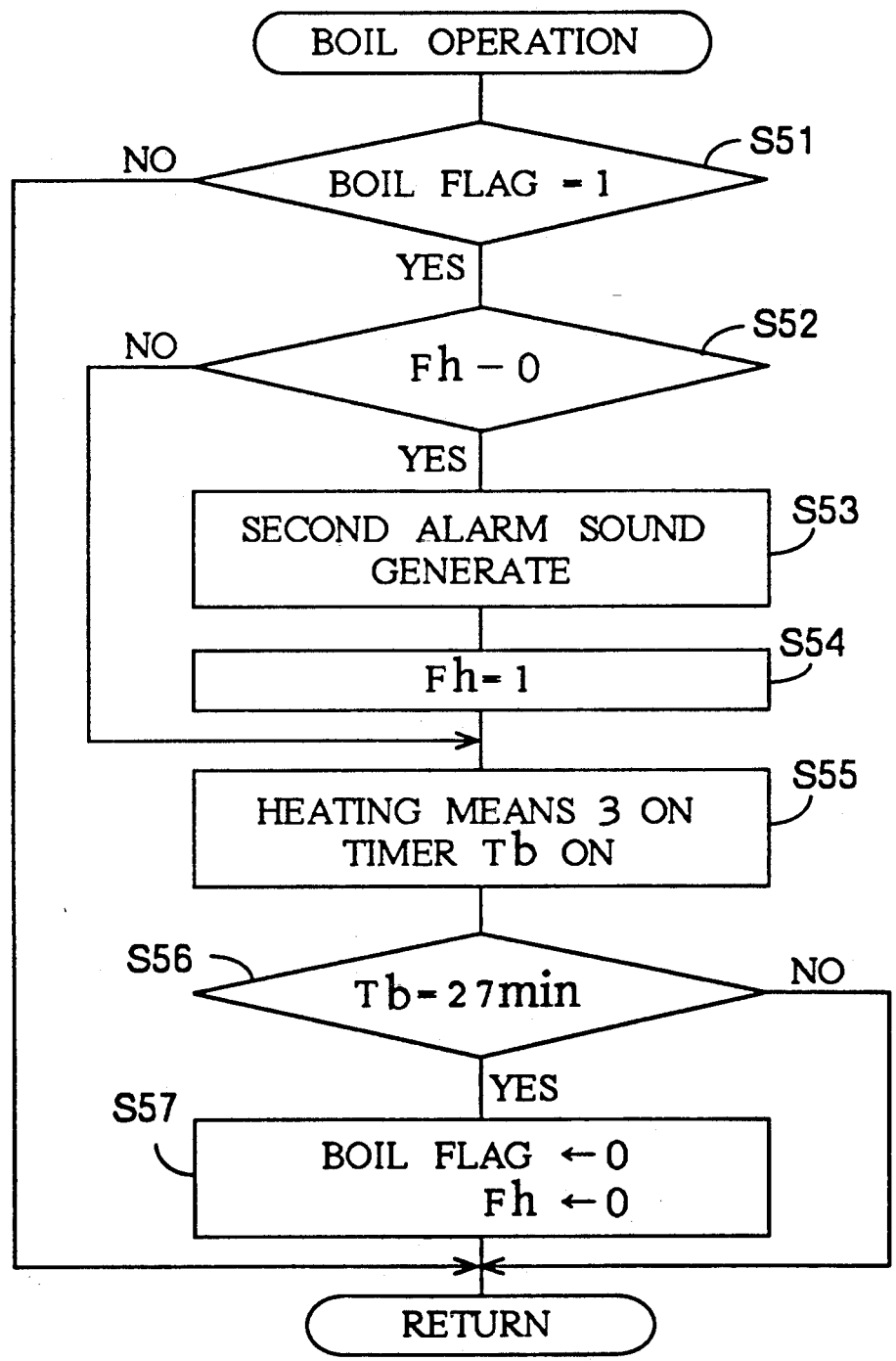

The boil operation is performed as shown in FIG. 15. Referring to FIG. 15, first of all a condition of a boil flag is judged in a step S51. If a setting of the boil flag is judged in the step S51 (the boil flag is "1"), a step S52 is performed and a condition of a boil alarm sound output flag Fh is judged. Now, if the setting of the boil flag is not judged in the step S51 (the boil flag is "0"), the step S52 is not performed and the sub routine for the boil operation is stopped so as to return to the main routine. In the step S52, if the setting of the boil alarm sound output flag Fh is not judged, a step S53 is performed and a signal is sent to the buzzer in order to generate a second alarm sound which warns a user a performance of the boil operation. Next, a step S54 is performed and the boil alarm sound output flag Fh is set (the boil alarm sound output flag Fh becomes "1"). Next, a step S55 is performed and the electric current is turned on for the heating means 3. Furthermore, in the step S55, a timer (Tb) which the operation controlling means 7 has built-in is started. Now, if the setting of the boil alarm sound output flag Fh is judged in the step S52, the steps S53, S54 are not performed and the step S55 is performed. Next, a step S56 is performed and a condition whether the electric current has been turned on for the heating means 3 for 27 minutes or not is judged. If the electric current has been turned on for the heating means 3 for 27 minutes, a step S57 is performed and the boil flag and the boil alarm sound output flag Fh are reset, respectively (the boil flag and the boil alarm sound output flag Fh are "0"). If the electric current is not turned on for the heating means 3 for 27 minutes, a step S57 is not performed and the sub routine for the boil operation is stopped so as to return to the main routine.

Figure 18:
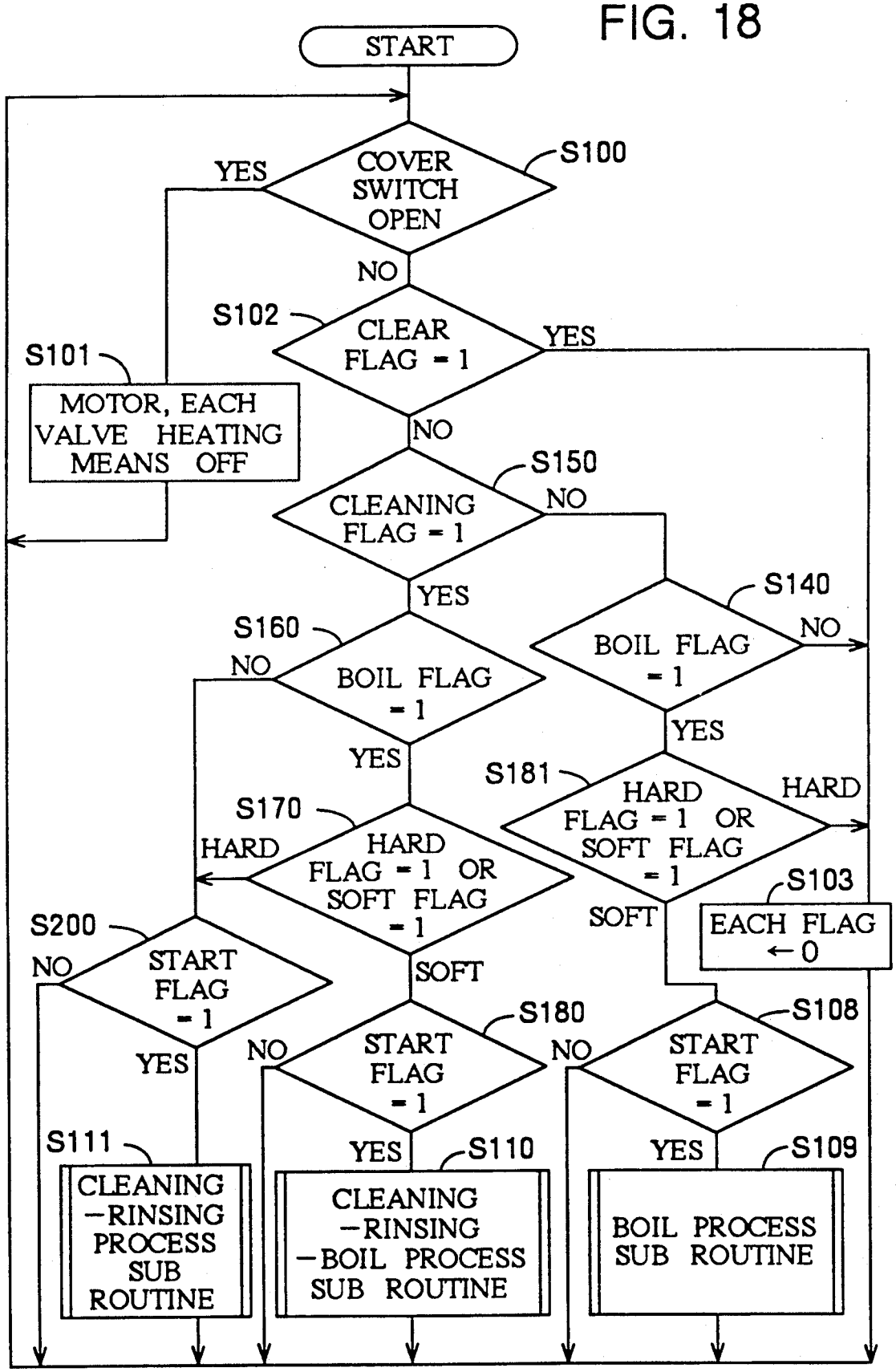
FIG. 18 is a flow chart of a main routine of an operation controlling means in an embodiment of a cleaning device for contact lenses in accordance with the present invention.

Next, the main routine of this cleaning device for contact lens is performed as follows. Referring to FIG. 18, first of all a condition of whether the cover switch 10 is closed or not is judged in a step S100. If the cover switch 10 is not closed, a step S101 is performed. In the step S101, the motor 2a is stopped and the electric current for the heating means 3 is interrupted. Furthermore, plural valves 4, 5, 6 are closed. Thereafter, the step 100 is performed repeatedly. If the cover switch 10 is closed, a step S102 is performed and a condition of a clearing flag is judged. In the step S102, if the setting of the clearing flag is judged (the clearing flag is "1"), a step S103 is performed and each flag corresponding to each switch (including the clearing switch) is reset (each flag corresponding to each switch becomes "0"), respectively. As a result, the flag corresponding to the changeover switch 81 is reset to the soft-range in the step S103. After the step S103 is performed, the step S100 is performed repeatedly.

In the step S102, if the clearing flag is not set (the clearing flag is not "1"), a step S150 is performed and a condition of the cleaning flag is judged. If the cleaning flag is not set (the cleaning flag is "0"), a step S140 is performed and a condition of the boil flag is judged. In the step S140, if the boil flag is not set (the boil flag is "0"), the step S103 is performed. If the boil flag is set (the boil flag is "1"), a step S181 is performed and a condition of a changeover flag is judged. In the step S181, if the hard-range is chosen, the step S103 is performed. On the other hand, in the step S181, if the soft-range is chosen, a step S108 is performed and a condition of a start flag is judged. If the start flag is not set (the start flag is "0"), the step S100 is performed repeatedly. In the step S108, if the start flag is set (the start flag is "1"), a step S109 is performed and the boil process sub routine is performed. After the boil process sub routine is performed, the step S100 is performed repeatedly.

On the other hand, if the cleaning flag is set (the cleaning flag is "1") in the step S150, a step S160 is performed and the condition of the boil flag is judged. If the boil flag is not set (the boil flag is "0"), a step S200 is performed and the condition of the start flag is judged. If the start flag is not set (the start flag is "0"), the step S100 is performed repeatedly. In the step S200, if the start flag is set (the start flag is "1"), a step S111 is performed and the cleaning-rinsing process sub routine is performed. After the cleaning-rinsing process sub routine is performed, the step S100 is performed repeatedly.

In the step 160, if the boil flag is set (the boil flag is "1"), the condition of the changeover flag is judged in a step S170. In the step S170, if the hard-range is chosen, the step S200 is performed. On the other hand, in the step S170, if the soft-range is chosen, a step S180 is performed and a condition of a start flag is judged. If the start flag is not set (the start flag is "0") , the step S100 is performed repeatedly. In the step S180, the start flag is set (the start flag is "1"), a step S110 is performed and the cleaning-rinsing-boil process sub routine is performed. When the cleaning-rinsing-boil process sub routine is performed, the step S100 is performed repeatedly.

Now, each process sub routine is constituted by a combination of above-described operation sub routines in accordance with the flow diagram as shown in FIG. 17. As an example of the process sub routine, a timing chart of the cleaning-rinsing-boil process is shown in FIG. 19. Now, the start flag and the exchange flag are reset (the start flag and the exchange flag become "0") when each process sub routine is ended in the steps S109, S110, S111.

Furthermore, a pressure relief valve (not shown) which communicates the cleaning chamber with the outside is disposed so as to prevent excess pressure during the boil operation.

As mentioned above, according to this embodiment, since the feeding amount in the first and second rinsing processes C2 is controlled by the feeding timer which the operation controlling means 7 has built-in, as compared with a control by the liquid level sensor, it is possible to reduce the manufacturing cost and it is possible to miniaturize the cleaning device for contact lenses.

Furthermore, in this embodiment, a bar-shaped electric conductor (a stainless-bar 21) is coated with PTFE resin on all outer circumferential surfaces thereof. Thus, even though the liquid level is near a border between the top portion of the stainless steel bar 21 and the PTFE resin, the conductor will remain effectively insulated by the PTFE resin.

Furthermore, in this embodiment, the cylindrical case 31 of the heating means 3 is adopted as the electric terminal. Therefore, it is not necessary to provide a separate electric terminal and it is possible to simplify the structure. Namely, the nichrome exothermic wire (not shown) of the heating means 3 is insulated and is received in the metallic cylindrical case 31 in order to provide heat. Furthermore, the cylindrical case 31 is grounded in order to prevent electric leakage. Accordingly, if the cylindrical case 31 is an electric terminal, it is possible to constitute the liquid level sensor by one bar-shaped electric conductor 21 coated with PTFE resin and one output signal wire connected with the bar-shaped electric conductor. A full level signal will issue only when the liquid level reaches the top of the conductor 21 and provides electrical continuity with the case 31 of heating means 3.

According to the present invention, the feeding amount in the feeding operation in the cleaning process Cl or the feeding operation in the final rinsing process C2 or the feeding operation in the boil process B is controlled to the same liquid level by this binary output type of liquid level sensor 20. Furthermore, the feeding amount in the feeding operation in the other rinsing processes is controlled to a lower liquid level by the feeding timer. Therefore, in the present invention, it is possible to obtain the following advantages.

(a) It is possible to reduce the feeding amount which is required in a rinsing operation. Furthermore, since the feeding amount of the last rinsing process is the high liquid level, it is possible to prevent the adherence of floating dirt and bubbles to the contact lens or the lens case. In all but the last rinsing process, it is not necessary to feed so as to sink the contact lens under the liquid level since the liquid level will rise during operation of the stirrer, and so it is possible to rinse the contact lens by a feeding amount which is smaller than a half of the feeding amount of the final rinsing operation. Because an object of the initial rinsing processes is the removal of dirt or bubbles from the contact lens, even though the feeding amount is changed as the liquid level in the feeding tank change, the feeding amount is not excessive or insufficient. Therefore, there are no drawbacks due to over-flow in the cleaning chamber or due to too little feeding amount.

Accordingly, it is possible to clean the contact lens with reduced liquid feed.

(b) Since the feeding amount in the feeding operation in the cleaning process or the feeding operation of the last rinsing process or the feeding operation in the boil process is controlled to same single liquid level by the binary output type of liquid level sensor, it is possible to simplify the structure of the feeding amount detecting means.

Now, instead of control by the liquid level sensor, it is possible to control the feeding amount by means of controlling the feeding time by the feeding timer (for example, that which the operation controlling means has built-in). According to this control, it is possible to simplify the structure of the feeding amount detecting means and it is possible to miniaturize the feeding amount detecting means. Since the liquid is fed from the feeding tank by gravity and is not fed by a feeding pump, however, even though the feeding time is constant, the feeding amount is changed by a change of the liquid level in the feeding tank. Therefore, when the liquid level in the feeding tank is high or low, the feeding amount is increased or decreased, respectively. However, this is not a problem since the cleaning chamber is not completely filled by the feeding process controlled by the timer. Moreover, it is not a problem in the cleaning process or the feeding operation of the last rinsing process or the feeding operation in the boil process since there control is not by the timer.

As mentioned above, according to the present invention, it is possible to provide an improved cleaning device for contact lenses which can decrease the consumption rate of the liquid without increasing the size of the device and complicating the structure of the device.

Furthermore, according to the present invention, since the cleaning device for contact lenses is provided with the liquid level sensor having the bar-shaped electric conductor which is coated with PTFE resin on all outer circumferential surfaces thereof and is vertically mounted in the cleaning chamber, it is possible to obtain the following advantages.

(c) In the present invention, as compared with prior electric terminal bar-type of liquid sensor, it is unnecessary to fix the electric terminal to the pivoting cover member and it is possible to fix the electric terminal. Furthermore, it is unnecessary to extend the insulated wires from the cover member toward a housing. Furthermore, the electrode-bar does not disturb the operation of maintenance when the cover member is opened. Furthermore, as compared with the conventional capacitive type liquid level sensor, it is possible to simplify a circuit for processing an electric signal.

(d) In the present invention, when an electric current flows from the top portion of the bar-shaped electric conductor and the electric terminal which is in the lower portion of the heater via the liquid, the feeding operation is interrupted. Therefore, it is possible to minutely control the feeding amount. Furthermore, when the electric current is interrupted, this interruption is detected as an abnormal drop of the liquid level. Thereby, the electric current for the heating means is interrupted and it is possible to prevent an empty heating of the heating means. Namely, in the present invention, the liquid sensor functions as a sensor for controlling the feeding amount and as a switch for preventing an empty heating of the heating means.

(e) It is possible to simplify the structure of the liquid level sensor and it is possible to simplify the maintenance. Furthermore, it is possible to miniaturize the liquid level sensor.

As mentioned above, according to the present invention, it is possible to provide an improved cleaning device for contact lenses which can minutely control the feeding amount of the liquid without increasing the device size and complicating the structure of the device.

The principles, preferred embodiment and modes of operation of the present invention have been described in the foregoing application. The invention which is intended to be protected herein should not, however, be construed as limited to the particular forms disclosed, as these are to be regarded as illustrative rather than restrictive. Variations and changes may be made by those skilled in the art without departing from the spirit of the present invention. Accordingly, the foregoing detailed description should be considered exemplary in nature and not limited to the scope and spirit of the invention as set forth in appended claims.

What is claimed as new and desired to be secured by Letters Patent of the United States is:

1. A cleaning device for contact lenses comprising;
   a housing having a cleaning chamber which receives contact lens therein,
   stirring means for generating a liquid flow within the cleaning chamber,
   heating means for boiling a liquid in the cleaning chamber,
   feeding means for feeding the liquid into the cleaning chamber,
   discharging means for discharging the liquid out of the cleaning chamber,
   feeding amount detecting means for detecting a feeding amount of the liquid which is fed into the cleaning chamber, and
   operation controlling means for controlling the stirring means, the heating means, the feeding means and the discharging means in response to a feeding amount of the liquid detected by the feeding amount detecting means, so as to perform a cleaning process, plural rinsing processes and a boil process,
   wherein said feeding amount detecting means comprises a binary output liquid level sensor which detects a single liquid level, means for using said binary output sensor to set a first feeding amount in the cleaning process, a last rinsing process and the boil process, and wherein the feeding amount detecting means further comprises a feeding timer which detects a feeding time and means for using said feeding timer for controlling a second feeding amount in at least one other rinsing process such that the second feeding amount is smaller than the first feeding amount.

2. A cleaning device for contact lens as recited in claim 1, wherein the feeding means includes a feeding tank which is positioned so as to be higher than a full liquid level of the cleaning chamber and means for feeding the liquid to the cleaning chamber by gravity, and wherein the discharging means includes a discharging tank which is positioned so as to be lower than a lowermost liquid level of the cleaning chamber and means for discharging the liquid from the cleaning chamber to the discharging tank.

3. A cleaning device for contact lens as recited in claim 2, wherein the binary output liquid level sensor comprises a bar-shaped electric conductor which is coated with insulating material on all outer circumferential surfaces thereof but is not coated at a top thereof, and which is disposed in the cleaning chamber, and an electric terminal which is disposed in the cleaning chamber at a position lower than the top of the bar-shaped electric conductor, wherein an electric current can flow from said conductor to said terminal when the cleaning chamber is full.

4. A cleaning device for contact lens as recited in claim 3, wherein the insulating material is PTFE resin.

5. A cleaning device for contact lens as recited in claim 3, wherein the electric terminal is comprised of a metallic outer tube portion of the heating means.

* * * * *